(12) United States Patent
Haeseler et al.

(10) Patent No.: US 8,112,259 B2
(45) Date of Patent: Feb. 7, 2012

(54) METHOD OF PREDICTING CHANGES IN THE CHEMICAL COMPOSITION OF A RESERVOIR OIL AS A RESULT OF BIODEGRADATION

(75) Inventors: Frank Haeseler, La Garenne Colombes (FR); Françoise Behar, Paris (FR)

(73) Assignee: IFP, Cedex (FR)

( * ) Notice: Subject to any disclaimer, the term of this patent is extended or adjusted under 35 U.S.C. 154(b) by 371 days.

(21) Appl. No.: 12/533,079

(22) Filed: Jul. 31, 2009

(65) Prior Publication Data

US 2010/0076735 A1    Mar. 25, 2010

(30) Foreign Application Priority Data

Aug. 1, 2008    (FR) ..................... 08 04435

(51) Int. Cl.
*G06G 7/50*    (2006.01)
*G06G 7/48*    (2006.01)
(52) U.S. Cl. ..................... 703/9; 703/2; 703/10; 703/12
(58) Field of Classification Search ................... 703/2, 9, 703/10, 12
See application file for complete search history.

(56) References Cited

FOREIGN PATENT DOCUMENTS

| FR | 2 830 646 A1 | 4/2003 |
| FR | 2 888 251 A1 | 1/2007 |

OTHER PUBLICATIONS

Huang et al. "Dissolved Oxygen Imaging in a Porous Medium to Investigate Biodegradation in a Plume with Limited Electron Acceptor Supply.", Environmental Science Technology 2003, 37, 1905-1911.*
French Search Report, FR 0804435, Dated Feb. 18, 2009.
Head, et al., "Biological activity in the deep subsurface and the origin of heavy oil", Nature, vol. 426, Nov. 2003.
Carpentier et al, "New Concepts for Biodegradation Evaluation in Oil fields, a Combined Geological and Numerical Approach", AAPG Annual Meeting, Mar. 10-13, 2002, Houston Texas.

* cited by examiner

*Primary Examiner* — Saif Alhija
(74) *Attorney, Agent, or Firm* — Antonelli, Terry, Stout & Kraus, LLP.

(57) ABSTRACT

Method of determining the compositional evolution of fluids present in a porous medium as a result of biodegradation.

A biodegradation compositional scheme is defined from twelve chemical classes allowing the hydrocarbons and the gases resulting from biodegradation to be described. The initial amount of each one of these chemical classes contained in the fluids before biodegradation is determined. A reaction scheme is then defined for biodegradation, wherein the chemical classes react with electron acceptors according to parallel reactions having different velocities, and each class reacts with these acceptors according to sequential reactions. The biodegradation reaction velocities are determined for each class. The composition of the fluids is then deduced by assessing the amount of each chemical class by applying the reaction scheme. The composition of the biodegraded hydrocarbons, as well as the amount of acid gas and of methane produced, are notably deduced.

Application: notably petroleum reservoir development.

11 Claims, 2 Drawing Sheets

METHOD OF PREDICTING CHANGES IN THE CHEMICAL COMPOSITION OF A RESERVOIR OIL AS A RESULT OF BIODEGRADATION

FIELD OF THE INVENTION

The present invention relates to the sphere of petroleum industry. It concerns a method for evaluating the biodegradation of hydrocarbons present in a geological structure such as a petroleum reservoir, as a result of the action of a bacterial population.

The method according to the invention provides a very useful evaluation tool, notably for geologists eager to direct their investigations outside risk zones. In particular, it can be used in the technical field of basin modeling to predict the amount and the quality of the oil that can be expected in connection with the biological alteration that can occur in such environments.

One problem that is commonly encountered when defining the interest of a petroleum objective, i.e. an undrilled hydrocarbon trap, located at a relatively low temperature (usually below 80° C.) is the assessment of the "biodegradation" risk.

In fact, it is commonly recognized that biodegradation, defined as the selective destruction of part of the molecules that make up a petroleum crude by bacteria, can develop up to temperatures that can reach 70° C. to 80° C. Such temperatures are common in particular in marine sediments, which are zones where oil prospecting is currently the most active.

This biodegradation has the effect of modifying the quality of the oil. This quality is measured by the viscosity and the API degree that is inversely proportional to the density. It depends on the composition of the oil (API degree scale between 0 and 40). A high proportion of light hydrocarbons increases the API degree, whereas a high proportion of resins and asphaltenes (NSOs) decreases the API degree. During the geological history of a fluid, thermal maturation tends to lighten reservoir oils and therefore to increase the API degree, while the microbial alteration tends to weight up the oil and therefore to decrease its API degree (Conan et al. 1979 Advances in Organic Geochemistry, Pegamon Press Oxford 1-17 and Peters and Moldowan, 1993, The biomarker guide, Prentice Hall).

Another problem induced by the biodegradation of hydrocarbons is the production of gas (methane and acid gas: $CO_2$ and $H_2S$). Some of these gases have an economic value (case of methane) and others reduce the economic value of the reservoir ($H_2S$).

Biodegradation is a biological phenomenon that can affect the amount and the chemical composition of reservoir oils. The bacteria responsible for these reactions are present in the porous medium and live in the water that circulates in the porous medium. These bacteria use the hydrocarbons as a source of carbon and energy for their development and preservation. They thus, on the one hand, selectively degrade some hydrocarbons and therefore modify both the amount and the composition of the oil in place and, on the other hand, they generate metabolites such as gaseous species ($CH_4$, $H_2S$ and $CO_2$) and new chemical structures such as carboxylic acids. However, the acids generated are in turn degraded and they represent in fact only a small part of the residual biodegraded oils. For the bacteria to live, the system also requires ingredients such as electron acceptors and nutriments. Biological reactions need nutriments such as phosphorus and nitrogen, as well as metals, which are essential for the synthesis of the molecules that make up the bacteria. Their absence means bacterial growth arrest.

The biodegradation process can be described as follows. The micro-organisms present in the porous media use the energy and carbon source provided by some hydrocarbon families present in the reservoir oils, with two goals:

develop and produce as much biomass as possible as long as the nitrogen and the phosphorus are not depleted and the trace elements such as metals are no limiting factors, maintain, i.e. use the energy available through degradation reactions that generate no additional biomass. During such reactions, the hydrocarbons are actually degraded and metabolites are generated, but no biomass increase is observed.

Thus, in the petroleum industry, it is very important to know the role of biodegradation in order to know the quality and the amount of oil expected in a sedimentary basin. In fact, biodegradation is a major risk for oil companies whose deep sea drilling operations represent a considerable financial investment. Any method allowing this risk to be reduced is therefore of major interest for these companies. A method allowing the effect of biodegradation on the amount and the quality of the oil to be assessed is therefore required.

BACKGROUND OF THE INVENTION

Some authors have been able to assess degradation kinetics by correlating oil residence times in the subsoil with the biodegradation level (Larter et al, 2003 Organic Geochemistry 4, 6001-613, Behar et al, 2006, Organic Geochemistry 37, 1042-1051 et de Barros Penteado et al, 2007, Organic Geochemistry 38, 1197-1211). It essentially consists of a descriptive work that aims to record the biodegradation and its consequences, and to determine specific biodegradation rates for some basins. In particular, Larter's work allows to predict a biodegradation rate without taking account of the oil composition, this rate being mainly applied to saturated hydrocarbons. Besides, the mainspring of biodegradation is the diffusion of hydrocarbons in the water/oil contact zone, insofar as this contact zone provides the source of electron acceptors.

A method of predictively assessing the oil biodegradation level in a basin is known from patent EP-1,436,412. This methodology is based on a statistical analysis of the number of bacteria present in the subsoil as a function of depth. Besides, the result of this approach is not compositional.

In general terms, the known methods aim either to describe the biodegradation and not to predict it, or to predict the biodegradation by taking account of the water/oil contact plane to control the biodegradation velocities. These types of method do not take account of factors limiting the activity of micro-organisms: the electron acceptors. Thus, these methods are not really predictive and they require calibration with well data.

The object of the invention thus relates to an alternative method of assessing the compositional evolution of hydrocarbons trapped in a porous medium as a result of biodegradation.

SUMMARY OF THE INVENTION

The invention relates to a method of determining a composition of fluids present in a porous medium after biodegradation. It comprises the following stages:

defining a biodegradation compositional scheme from at least the following chemical classes: $CO_2$, n-saturated $H_2S$, $C_1$, $C_2$-$C_4$, $C_6$-$C_{14}$ and iso-saturated $C_6$-$C_{14}$, cyclo-saturated $C_6$-$C_{14}$, $C_6$-$C_{14}$ aromatics, n-saturated $C_{14+}$, iso-saturated $C_{14+}$, cyclo-saturated $C_{14+}$, $C_{14+}$ aromatics, NSOs, determining an amount of each one of said chemical classes contained in said fluids before biodegradation, defining a biodegradation reaction scheme wherein said chemical classes react with electron acceptors and wherein it is imposed that said classes react simultaneously with a first electron acceptor having the highest oxydoreduction potential, according to different reaction velocities and up to depletion of said first acceptor in the medium, then they react sequentially towards the other electron acceptors according to the same principle, determining said reaction velocities of each one of said chemical classes according to at least:—the potential concentration of the chemical classes in the water;—their intrinsic biodegradability;—their reactivity to said electron acceptors;—the temperature of the medium; and—the residence time of said fluids within the medium, and determining the composition of said fluids by assessing an amount for each one of said chemical classes of the compositional scheme by applying the reaction scheme.

The electron acceptors can be selected from among the following acceptors: $O_2$, $NO_3$, $SO_4$ and $H_2O$.

According to the invention, the reaction velocities can be defined by a product of a first term ($R_t$) that allows an effect of the residence time in the porous medium to be taken into account, a second term ($R_T$) allowing an effect of the temperature to be taken into account and a third term ($V_c$) allowing the accessibility and the intrinsic biodegradability of each chemical class to be taken into account.

The first term, $R_t$, can represent a biodegradation efficiency and it can be determined by means of a first evolution curve of efficiency $R_t$ as a function of the residence time in the medium. This curve can be an exponential function of time, where efficiency $R_t$ is above 95% beyond about 2000 years.

The second term, $R_T$, can represent a biodegradation efficiency and it can be determined by means of a Gaussian evolution curve of efficiency $R_T$ as a function of the temperature in the medium. This Gaussian curve is advantageously centered on a temperature of about 30° C. and it is equated to zero for 0° C. and about 70° C.

The third term, $V_c$, can be determined by considering that the intrinsic biodegradability velocity of the saturated $C_6$-$C_{14}$ is higher than that of the other classes, and by considering that the maximum accessibility velocity of the $C_6$-$C_{14}$ aromatics is higher than that of the other classes.

Thus, the reaction velocities can be defined by:

$VC_{14}\text{-sat}=0.4 \times V_{max}$ $VC_{14}\text{-aro}=0.3 \times V_{max}$ $VC_{14+}n=0.2 \times V_{max}$ $VC_{14+}\text{iso}=0.18 \times V_{max}$ $VC_{14+}\text{cyclanes}=0.08 \times V_{max}$ $VC_{14+}\text{aro}=0.05 \times V_{max}$ $V\text{NSO}=0$ where $V_{max}$ is the maximum biodegradation velocity defined by the product of the maximum intrinsic biodegradability velocity by the maximum accessibility velocity.

According to an embodiment, the medium can be a petroleum reservoir, and an amount of acid gas produced upon biodegradation is deduced from the composition of the fluids in order to determine development conditions for the petroleum reservoir.

According to another embodiment, the medium can be a petroleum reservoir, and an amount of methane produced upon biodegradation is deduced from the composition of the fluids in order to determine development conditions for the petroleum reservoir.

BRIEF DESCRIPTION OF THE FIGURES

Other features and advantages of the method according to the invention will be clear from reading the description hereafter of embodiments given by way of non imitative example, with reference to the accompanying figures wherein.

DETAILED DESCRIPTION

The method according to the invention allows to assess the biodegradation of hydrocarbons present in a geological structure such as a petroleum reservoir. It consists in evaluating the evolution of the amount of chemical components contained in these hydrocarbons during migration of the hydrocarbons and filling of the structure (referred to as trap). This evaluation allows for example to determine whether it is appropriate to develop a petroleum reservoir, and the development conditions of this reservoir.

The method comprises the following stages:

1—defining a compositional scheme to describe the hydrocarbons and gases resulting from biodegradation, 2—estimating the amount of each chemical class of the compositional scheme present in the hydrocarbons before biodegradation, 3—defining a reaction scheme wherein the chemical classes react in parallel with electron acceptors and each chemical class reacts sequentially with the electron acceptors, 4—evaluating the evolution of the amount of each chemical class by means of the reaction scheme.

1—Biodegradation Compositional Scheme

The bacterial action that is the cause of the biodegradation of hydrocarbons generates non hydrocarbon gases ($CO_2$, $H_2S$) and methane ($CH_4$). It alters more rapidly the n-saturated hydrocarbons and the iso-saturated hydrocarbons. The saturated cyclic structures and the aromatics can then be affected. In principle, sulfur-containing and nitrogen-containing compounds (NSOs) remain unchanged, as well as $C_2$-$C_4$ gases, except under extreme conditions. Thus, the a priori order of alteration is as follows: sat $C_6$-$C_{14}$ and $C_6$-$C_{14}$ aromatics, saturated $C_{14+}$.

According to the invention, the following twelve chemical classes are used for compositional formalization of the biodegradation:

| | |
|---|---|
| Class 1 | $CO_2$ |
| Class 2 | $H_2S$ |
| Class 3 | $C_1$ |
| Class 4 | $C_2$-$C_4$ |
| Class 5 | n-saturated $C_6$-$C_{14}$ and iso-saturated $C_6$-$C_{14}$ |
| Class 6 | cyclo-saturated $C_6$-$C_{14}$ |
| Class 7 | $C_6$-$C_{14}$ aromatics |
| Class 8 | n-saturated $C_{14+}$ |

| | |
|---|---|
| Class 9 | Iso-saturated $C_{14+}$ |
| Class 10 | Cyclo-saturated $C_{14+}$ |
| Class 11 | $C_{14+}$ aromatics |
| Class 12 | NSOs | with the following conventional nomenclature:

$C_1$: hydrocarbon family with 1 carbon atom
$C_2$: hydrocarbon family with 2 carbon atoms
$C_3$: hydrocarbon family with 3 carbon atoms
$C_4$: hydrocarbon family with 4 carbon atoms
$C_6$-$C_{14}$ or $C_{14-}$: hydrocarbons having between 6 and 14 carbon atoms
$C_{14+}$: hydrocarbons having more than 14 carbon atoms
NSOs: heteroatomic compounds generally of high molecular mass (resins and asphaltenes) containing nitrogen, sulfur and oxygen functions.

Classes 3 to 12 allow to describe the hydrocarbons before and after biodegradation.

Classes 1 and 2 allow to take into account the generation of non hydrocarbon gas during biodegradation, which is important in order to determine the development conditions of a field.

2—Compositional Estimation Before Biodegradation

This type of estimation can be conventionally carried out from a tool known to specialists as "basin simulator" or "basin model". An example of a method used by this type of software tool is described in patent application FR-2,906,482. This application describes a method of modeling the thermal cracking of kerogen and associated petroleum products.

3—Biodegradation Reaction Scheme

The base unit for biodegradation calculations is the molar concentration $C_{mi}$ of the compounds i (chemical classes) taken into account in the compositional scheme. This molar concentration is defined by the formula presented in Equation (1).

$$C_{mi} = \frac{C_i}{M_i} \bigg/ \frac{C_o}{M_o} \quad (1)$$

with:
$C_i$: mass concentration of compound i
$M_i$: molar mass of compound i
$C_o$: mass concentration of the oil
$M_o$: molar mass of the oil.

The molar mass of the oil is a parameter that depends on the characteristics of the petroleum. Its value is a function of the type of kerogen that has caused genesis of the oil, of the thermal history of the petroleum system and in particular the secondary cracking that the petroleum may have undergone. The molar mass of the oil also depends on biodegradation, thus a biodegraded oil is heavier than it was before biodegradation.

$M_o = f(\text{Type I, II, III}).f(\text{thermal history}).f(\text{biodegradation})$ Mineralization of the hydrocarbons under the action of hydrocarbonoclastic bacteria leads, on the one hand, to the complete disappearance of the hydrocarbons initially present and, on the other hand, to the production of the following final metabolites:

$CO_2$ and $H_2O$ under aerobic conditions
$CO_2$, $H_2O$ and $N_2$ under denitrifying conditions
$CO_2$, $H_2O$ and $H_2S$ under sulfatoreducing conditions
$CO_2$ and $CH_4$ under methanogenic conditions.

These equations describe the hydrocarbon biodegradation pathways with different electron acceptors. They consist of aerobic biodegradation conditions (in the presence of oxygen), denitrifying conditions (in the presence of nitrate), sulfatoreducing conditions (in the presence of sulfate) and methanogenic conditions. This succession of mechanisms involving electron acceptors with an increasingly low oxydoreduction potential can be conducted only after depletion of the previous electron acceptor.

In natural systems, the biodegradation of hydrocarbons is partial. On the one hand, residual hydrocarbons always remain, at least as traces, and on the other hand metabolic intermediaries resistant to subsequent biodegradation are produced by bacteria and they can accumulate.

It is possible to write the overall hydrocarbon biodegradation equations (CxHy) by using a metabolite term in form of an organic acid or of a diol, which corresponds to the following chemical formula: $CxH(y-2)O_2$. A reaction of this type thus corresponds to a partial mineralization, to an incomplete biodegradation, even when all of the hydrocarbons disappear. The next equations leave aside the biomass formation that may be a (non imperative) consequence of biodegradation.

The energy that the bacteria can assimilate from the metabolism of their substrate depends on the oxydoreduction potential of the electron acceptor. A high oxydoreduction potential (case of oxygen and, to a lesser extent, of nitrate) allows high energy efficiency, whereas a low oxydoreduction potential (case of sulfate and of water) goes together with a more limited energy efficiency for the bacteria involved. It appears that the liposoluble metabolites accumulate when the oxydoreduction potential of the electron acceptors decreases. This phenomenon is linked with the limited energy efficiency. It can thus be observed that, upon biodegradation of the hydrocarbons in the environment, the concentration in oxygen compounds present in the residual oil phase tends to increase.

3a—Sequential and Overall Biodegradation Equations

According to the invention, the biodegradation reaction scheme can comprise a set of sequential reactions for each compound contained in the biodegraded hydrocarbon. These reactions are sequential stoichiometric reactions that have the advantage of involving a $C_xH_{(y-2)}O_2$ metabolite with a velocity v1 that disappears thereafter at a velocity v2. For each reaction, the absolute value of v1 in relation to that of v2 allows to determine the accumulation of the $C_xH_{(y-2)}O_2$ metabolite. This accumulation also depends on the overall yield of the reactions that can be incomplete under certain conditions. Velocity V corresponds to the overall reaction.

The sequential biodegradation equations of a hydrocarbon of formula CxHy with the main electron acceptors ($O_2$, $NO_3$, $SO_4$ and $H_2O$) are presented hereafter.

Electron Acceptor: $O_2$, Aerobic Biodegradation

Overall Equation:

Example $$C_{16}H_{34} + (49/2)O_2 \xrightarrow{V_{O_2}} 16\,CO_2 + 17\,H_2O.$$

Electron Acceptor: $NO_3$, Denitrification $$C_xH_y + NO_3 \xrightarrow{V1_{NO_3^{2-}}} C_xH_{(y-2)}O_2 + 1/2N_2 + H_2O$$

$$C_xH_{(y-2)}O_2 + (2/3x + 1/6y - 1)NO_3 \xrightarrow{V2_{NO_3^{2-}}}$$
$$xCO_2 + (1/3x + 1/12y - 1/2)N_2 + (1/2y - 1)H_2O$$

Overall Equation:

$$C_xH_y + (2/3x + 1/6y)NO_3 \xrightarrow{V_{NO_3^{2-}}} xCO_2 + (1/3x + 1/12y)N_2 + 1/2y\,H_2O$$

Example $$C_{16}H_{34} + (49/3)NO_3 \xrightarrow{V_{NO_3^{2-}}} 16\,CO_2 + (49/6)N_2 + 17\,H_2O$$

Electron Acceptor: $SO_4$, Sulfatoreduction $$C_xH_y + 13/10 SO_4 \xrightarrow{V1_{SO_4^{2-}}} C_{(x-1)}H_{(y-5)}O_2 + CO_2 + 13/10 H_2S + 6/5 H_2O$$

$$C_{(x-1)}H_{(y-5)}O_2 + (2/5x + 1/10y - 13/10)SO_4 \xrightarrow{V2_{SO_4^{2-}}}$$
$$(x-1)CO_2 + (2/5x + 1/10y - 13/10)H_2S + (-2/5x + 2/5y - 6/5)H_2O$$

Overall Equation:

$$C_xH_y + (2/5x + 1/10y)SO_4 \xrightarrow{V_{SO_4^{2-}}}$$
$$x\,CO_2 + (2/5x + 1/10y)H_2S + (-2/5x + 2/5y)H_2O$$

Example $$C_{16}H_{34} + (98/10)SO_4 \xrightarrow{V_{SO_4^{2-}}} 16\,CO_2 + (98/10)H_2S + (36/5)H_2O$$

Electron Acceptor: $H_2O$, Methanogenesis $$C_xH_y + 2H_2O \xrightarrow{V1_{H_2O}} C_xH_{(y-2)}O_2 + 3H_2$$

$$3H_2 + 3/4CO_2 + 3/4H_2O \xrightarrow{V_{H_2}} 3/4CH_4 + 9/4H_2O$$

$$C_xH_{(y-2)}O_2 + (x - 1/4y - 1/2)H_2O \xrightarrow{V2_{H_2O}}$$
$$(1/2x - 1/8y - 3/4)CO_2 + (1/2x + 1/8y - 3/4)CH_4$$

Overall Equation:

$$C_xH_y + (x - 1/4y)H_2O \xrightarrow{V_{H_2O}} (1/2x - 1/8y)CO_2 + (1/2x + 1/8y)CH_4$$

Example $$C_{16}H_{34} + (15/2)H_2O \xrightarrow{V_{H_2O}} (15/4)CO_2 + (49/4)CH_4$$

Thus, the biodegradation reaction scheme according to the invention is defined by the following set of chemical reactions:

for each chemical class present in the hydrocarbons, the reactions with the electron acceptors (oxygen, nitrate, sulfate or $H_2O$) are sequential: each class reacts with the electron acceptor having the highest oxydoreduction potential, up to depletion of this acceptor, then it reacts with the electron acceptor remaining in the medium and having the highest oxydoreduction potential. This mechanism can be repeated up to depletion of the electron acceptors, the chemical classes react in parallel: there is no sequential mechanism wherein a chemical class would react once another class has stopped reacting. In fact, all the classes can react at the same time, but with different kinetics.

Complete definition of this reaction scheme requires defining the different reaction velocities (V1 and V2 for the sequential reactions, or V for the overall reaction) for each chemical class.

3b—Expressions of the Biodegradation Velocities

The biodegradation velocity equation can be written as follows:

$$V_i = -\frac{\partial C_{mi}}{\partial t} = -\frac{C_{mi}(t_n) - C_{mi}(t_{n-1})}{t_n - t_{n-1}}$$

with:

$C_{mi}$: molar concentration of compound i that undergoes biodegradation $C_{mi}(t_n)$: molar concentration of compound i at the time $t_n$ $C_{mi}(t_{n-1})$: molar concentration of compound i at the time $t_{n-1}$ This velocity $V_i$ is, among other things, a function of the electron acceptor, of the biomass, of compound i, of temperature T, of the fluid hydrodynamics and of the diffusion.

The electron acceptors are: $O_2$, $NO_3$, $SO_4$, $H_2O$. This parameter depends on the reservoir type. The biomass concerns the nutrient elements (N, P, K) and the trace elements (Fe, Mg, Co . . . ). This parameter also depends on the reservoir type. Compound i is one of the chemical classes defined in the compositional scheme of stage 1. Temperature T is taken into account at a given time (temperature at the time of the reaction), but also according to the thermal history (paleosterilization). The hydrodynamics relates to the displacement of the oil in the reservoir and/or in the migration paths, to the evolution of the oil/water contact and to the water flow rate.

Depending on the electron acceptors, we can thus write:

$O_2$

For equation $$C_xH_y + O_2 \xrightarrow{V1} C_xH_yO_2,$$

we can write:

$$V1(O_2)_{C_6-C_{14}sat} = \frac{\partial C_{mC_xH_y}}{\partial t} = \frac{C_{mC_xH_y}(t_n) - C_{mC_xH_y}(t_{n-1})}{t_n - t_{n-1}}$$

$$V1(O_2)_{C_6-C_{14}sat} = \frac{\partial C_{mO_2}}{\partial t} = \frac{C_{mO_2}(t_n) - C_{mO_2}(t_{n-1})}{t_n - t_{n-1}}$$

$$V1(O_2)_{C_6-C_{14}sat} = -\frac{\partial C_{mC_xH_yO_2}}{\partial t} = -\frac{C_{mC_xH_yO_2}(t_n) - C_{mC_xH_yO_2}(t_{n-1})}{t_n - t_{n-1}}$$

And for equation $$C_xH_yO_2 + (x + 1/4y - 1)O_2 \xrightarrow{V2} xCO_2 + 1/2x\, H_2O,$$

we can write:

$$V2(O_2)_{C_6-C_{14}sat} = \frac{\partial C_{mC_xH_yO_2}}{\partial t} = \frac{C_{mC_xH_yO_2}(t_n) - C_{mC_xH_yO_2}(t_{n-1})}{t_n - t_{n-1}}$$

$$V2(O_2)_{C_6-C_{14}sat} = \frac{\partial C_{mO_2}}{\partial t} = \frac{C_{mO_2}(t_n) - C_{mO_2}(t_{n-1})}{t_n - t_{n-1}}$$

$$V2(O_2)_{C_6-C_{14}sat} = -\frac{\partial C_{mCO_2}}{\partial t} = -\frac{C_{mCO_2}(t_n) - C_{mCO_2}(t_{n-1})}{t_n - t_{n-1}}$$

$$V2(O_2)_{C_6-C_{14}sat} = -\frac{\partial C_{mH_2O}}{\partial t} = -\frac{C_{mH_2O}(t_n) - C_{mH_2O}(t_{n-1})}{t_n - t_{n-1}}$$

$NO_3$

For equation $$C_xH_y + 2/3\, NO_3 \xrightarrow{V1} C_xH_yO_2 + 4/3\, N_2$$

we can write:

$$V1(NO_3)_{C_6-C_{14}sat} = \frac{\partial C_{mC_xH_y}}{\partial t} = \frac{C_{mC_xH_y}(t_n) - C_{mC_xH_y}(t_{n-1})}{t_n - t_{n-1}}$$

$$V1(NO_3)_{C_6-C_{14}sat} = \frac{\partial C_{mNO_3}}{\partial t} = \frac{C_{mNO_3}(t_n) - C_{mNO_3}(t_{n-1})}{t_n - t_{n-1}}$$

$$V1(NO_3)_{C_6-C_{14}sat} = -\frac{\partial C_{mC_xH_yO_2}}{\partial t} = -\frac{C_{mC_xH_yO_2}(t_n) - C_{mC_xH_yO_2}(t_{n-1})}{t_n - t_{n-1}}$$

$$V1(NO_3)_{C_6-C_{14}sat} = -\frac{\partial C_{mN_2}}{\partial t} = -\frac{C_{mN_2}(t_n) - C_{mN_2}(t_{n-1})}{t_n - t_{n-1}}$$

And for equation $$C_xH_yO_2 + (2/3x + 1/6y - 2/3)NO_3 \xrightarrow{V2} xCO_2 + 1/2yH_2O + (1/3x + 1/12y - 1/3)N_2$$

we can write:

$$V2(NO_3)_{C_6-C_{14}sat} = \frac{\partial C_{mC_xH_yO_2}}{\partial t} = \frac{C_{mC_xH_yO_2}(t_n) - C_{mC_xH_yO_2}(t_{n-1})}{t_n - t_{n-1}}$$

$$V2(NO_3)_{C_6-C_{14}sat} = \frac{\partial C_{mNO_3}}{\partial t} = \frac{C_{mNO_3}(t_n) - C_{mNO_3}(t_{n-1})}{t_n - t_{n-1}}$$

$$V2(NO_3)_{C_6-C_{14}sat} = -\frac{\partial C_{mCO_2}}{\partial t} = -\frac{C_{mCO_2}(t_n) - C_{mCO_2}(t_{n-1})}{t_n - t_{n-1}}$$

$$V2(NO_3)_{C_6-C_{14}sat} = -\frac{\partial C_{mH_2O}}{\partial t} = -\frac{C_{mH_2O}(t_n) - C_{mH_2O}(t_{n-1})}{t_n - t_{n-1}}$$

$$V2(NO_3)_{C_6-C_{14}sat} = -\frac{\partial C_{mN_2}}{\partial t} = -\frac{C_{mN_2}(t_n) - C_{mN_2}(t_{n-1})}{t_n - t_{n-1}}$$

$SO_4$

For equation $$C_xH_y + 5/4\, H_2O + 5/4\, SO_4 \xrightarrow{V1} C_{(x-1)}H_yO_2 + CO_2 + 5/4\, H_2S,$$

we can write:

$$V1(SO_4)_{C_6-C_{14}sat} = \frac{\partial C_{mC_xH_y}}{\partial t} = \frac{C_{mC_xH_y}(t_n) - C_{mC_xH_y}(t_{n-1})}{t_n - t_{n-1}}$$

$$V1(SO_4)_{C_6-C_{14}sat} = \frac{\partial C_{mSO_4}}{\partial t} = \frac{C_{mSO_4}(t_n) - C_{mSO_4}(t_{n-1})}{t_n - t_{n-1}}$$

$$V1(SO_4)_{C_6-C_{14}sat} = \frac{\partial C_{mH_2O}}{\partial t} = -\frac{C_{mH_2O}(t_n) - C_{mH_2O}(t_{n-1})}{t_n - t_{n-1}}$$

$$V1(SO_4)_{C_6-C_{14}sat} = -\frac{\partial C_{mC_xH_yO_2}}{\partial t} = -\frac{C_{mC_xH_yO_2}(t_n) - C_{mC_xH_yO_2}(t_{n-1})}{t_n - t_{n-1}}$$

$$V1(SO_4)_{C_6-C_{14}sat} = -\frac{\partial C_{mCO_2}}{\partial t} = -\frac{C_{mCO_2}(t_n) - C_{mCO_2}(t_{n-1})}{t_n - t_{n-1}}$$

$$V1(SO_4)_{C_6-C_{14}sat} = -\frac{\partial C_{mH_2S}}{\partial t} = -\frac{C_{mH_2S}(t_n) - C_{mH_2S}(t_{n-1})}{t_n - t_{n-1}}$$

And for equation $$C_{(x-1)}H_yO_2 + (2/5x + 1/10y - 2/5)SO_4 \xrightarrow{V2}$$
$$(x-1)CO_2 + (y-x+1)H_2O + (2/5x + 1/10y - 2/5)H_2S,$$

we can write:

$$V2(SO_4)_{C_6-C_{14}sat} = \frac{\partial C_{mC_xH_yO_2}}{\partial t} = \frac{C_{mC_xH_yO_2}(t_n) - C_{mC_xH_yO_2}(t_{n-1})}{t_n - t_{n-1}}$$

$$V2(SO_4)_{C_6-C_{14}sat} = \frac{\partial C_{mSO_4}}{\partial t} = \frac{C_{mSO_4}(t_n) - C_{mSO_4}(t_{n-1})}{t_n - t_{n-1}}$$

$$V2(SO_4)_{C_6-C_{14}sat} = -\frac{\partial C_{mCO_2}}{\partial t} = -\frac{C_{mCO_2}(t_n) - C_{mCO_2}(t_{n-1})}{t_n - t_{n-1}}$$

$$V2(SO_4)_{C_6-C_{14}sat} = \frac{\partial C_{mH_2O}}{\partial t} = \frac{C_{mH_2O}(t_n) - C_{mH_2O}(t_{n-1})}{t_n - t_{n-1}}$$

$$V2(SO_4)_{C_6-C_{14}sat} = -\frac{\partial C_{mH_2S}}{\partial t} = -\frac{C_{mH_2S}(t_n) - C_{mH_2S}(t_{n-1})}{t_n - t_{n-1}}$$

$CH_4$

For equation $$C_xH_y + 2H_2O \xrightarrow{V1} C_xH_yO_2 + H_2,$$

we can write:

$$V1(CH_4)_{C_6-C_{14}sat} = \frac{\partial C_{mC_xH_y}}{\partial t} = \frac{C_{mC_xH_y}(t_n) - C_{mC_xH_y}(t_{n-1})}{t_n - t_{n-1}}$$

$$V1(CH_4)_{C_6-C_{14}sat} = \frac{\partial C_{mH_2O}}{\partial t} = -\frac{C_{mH_2O}(t_n) - C_{mH_2O}(t_{n-1})}{t_n - t_{n-1}}$$

$$V1(CH_4)_{C_6-C_{14}sat} = -\frac{\partial C_{mC_xH_yO_2}}{\partial t} = -\frac{C_{mC_xH_yO_2}(t_n) - C_{mC_xH_yO_2}(t_{n-1})}{t_n - t_{n-1}}$$

$$V1(CH_4)_{C_6-C_{14}sat} = -\frac{\partial C_{mH_2}}{\partial t} = -\frac{C_{mH_2}(t_n) - C_{mH_2}(t_{n-1})}{t_n - t_{n-1}}$$

And for equation $$C_xH_yO_2 + 2/3(1-y)H_2O \xrightarrow{V2} 1/3(4-y)CO_2 + (x + 1/3y - 4/3)CH_4,$$

we can write:

$$V2(CH_4)_{C_6-C_{14}sat} = \frac{\partial C_{mC_xH_yO_2}}{\partial t} = \frac{C_{mC_xH_yO_2}(t_n) - C_{mC_xH_yO_2}(t_{n-1})}{t_n - t_{n-1}}$$

$$V2(CH_4)_{C_6-C_{14}sat} = \frac{\partial C_{mH_2O}}{\partial t} = -\frac{C_{mH_2O}(t_n) - C_{mH_2O}(t_{n-1})}{t_n - t_{n-1}}$$

$$V2(CH_4)_{C_6-C_{14}sat} = -\frac{\partial C_{mCO_2}}{\partial t} = -\frac{C_{mCO_2}(t_n) - C_{mCO_2}(t_{n-1})}{t_n - t_{n-1}}$$

$$V2(CH_4)_{C_6-C_{14}sat} = -\frac{\partial C_{mCH_4}}{\partial t} = -\frac{C_{mCH_4}(t_n) - C_{mCH_4}(t_{n-1})}{t_n - t_{n-1}}$$

The above equations are written for $C_6$-$C_{14}$ sat, but they are absolutely identical for the other pseudocomponents $C_6$-$C_{14}$ aro, $C_{14}$+ sat and $C_{14}$+ aro.

3c—Determination of the Overall Biodegradation Velocities

According to the invention, the overall reactions are preferably used. A velocity is assigned to each one of them depending on the chemical class and the electron acceptor. These reaction velocities are referred to as overall velocities.

Thus, the overall velocities of each chemical class of the compositional scheme are determined according, on the one hand, to the hydrocarbon accessibility to bacteria, i.e. their potentially water soluble concentration and, on the other hand, to their intrinsic biodegradability (capacity of microorganisms to degrade them).

Such an overall velocity is considered to be the product of three terms: a first term ($R_t$) that allows the effect of the residence time in the porous medium to be taken into account, a second term ($R_T$) that allows the effect of temperature to be taken into account, and a third term ($V_c$) that allows the specific features of each chemical class to be taken into account.

Figure 1:
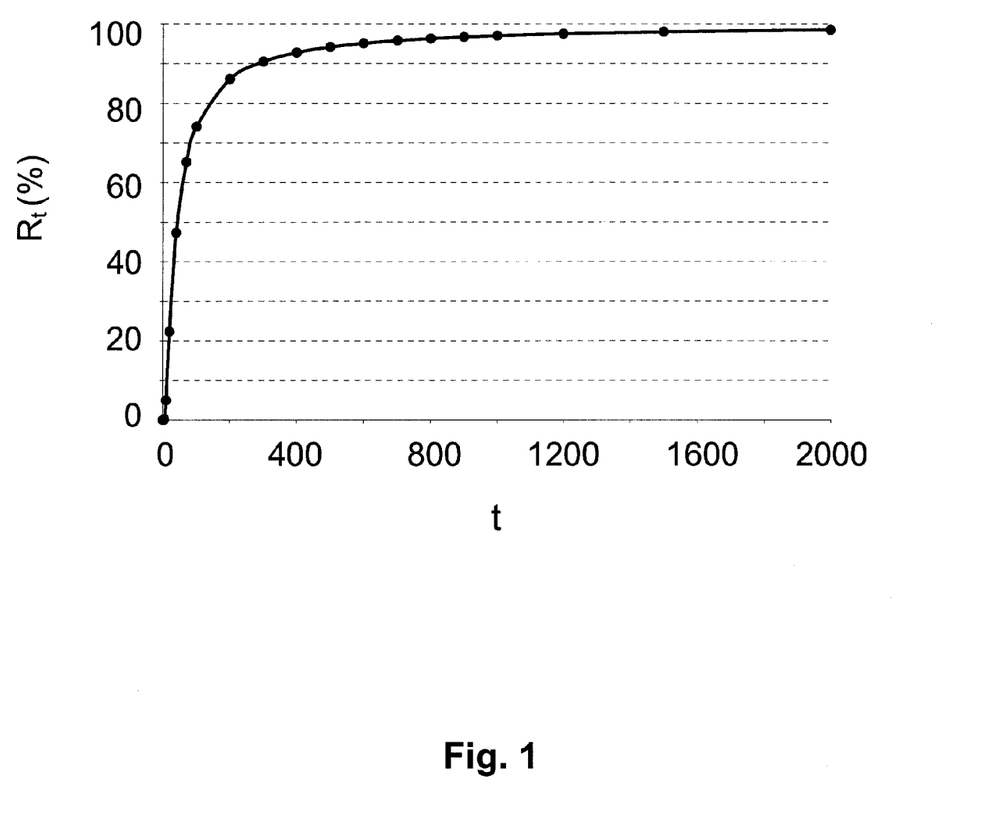
FIG. 1 illustrates the evolution, as a function of time t, of term $R_t$ allowing the effect of the residence time in the porous medium to be taken into account in the overall biodegradation velocity.

The first term ($R_t$) allowing the effect of the residence time in the porous medium to be taken into account represents a biodegradation efficiency. It can be determined from the curve shown in FIG. 1, which illustrates the evolution of the biodegradation efficiency $R_t$ (%) as a function of time t (in years). A plateau time (2000 years here) above which the efficiency is higher than 95% and below which the efficiency is all the lower as the time decreases is defined in this figure.

Figure 2:
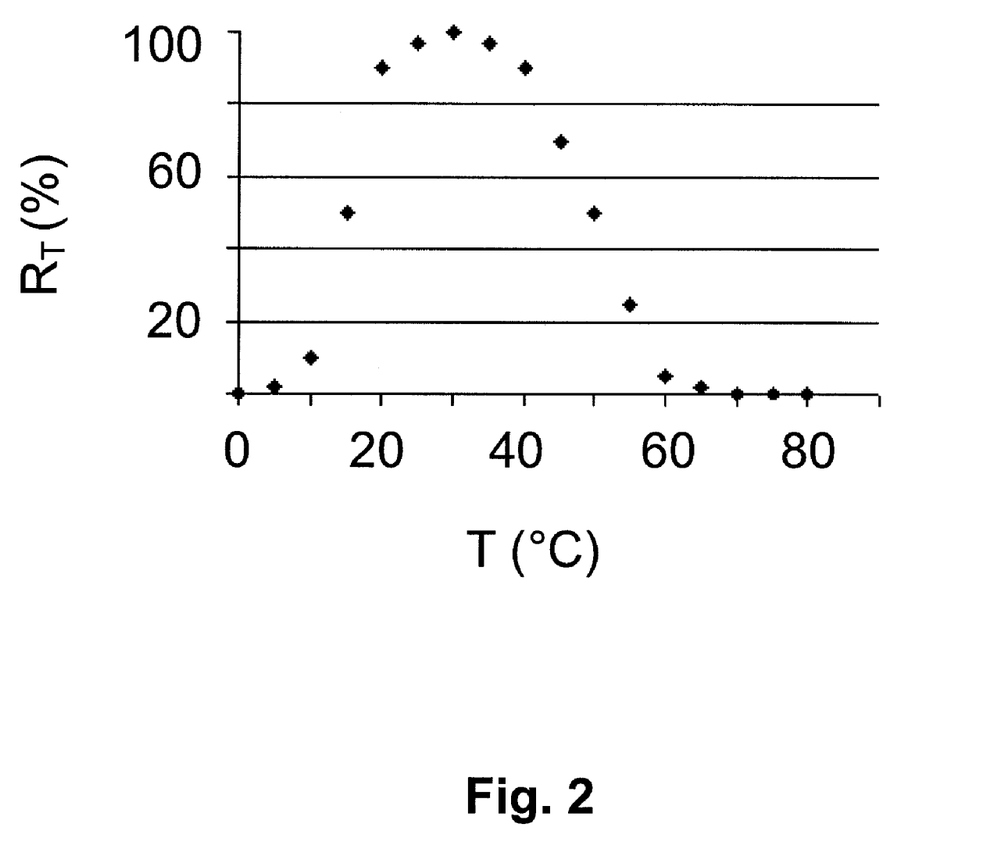
FIG. 2 illustrates the evolution, as a function of temperature T, of term $R_T$ allowing the effect of the temperature to be taken into account in the overall biodegradation velocity.

The second term ($R_T$) allowing the effect of temperature to be taken into account represents an overall biodegradation efficiency. It can be determined by considering that overall efficiency $R_T$ evolves as a function of temperature according to a Gaussian curve. According to an example illustrated in FIG. 2, this Gaussian curve is centered on a temperature of about 30° C. and it is equated to zero for 0° C. and approximately 70° C.

The third term ($V_c$) allowing the specific features of each chemical class to be taken into account consists of two terms. A first one accounts for the intrinsic biodegradability of the various compound classes. If $V_{bio}$ is the maximum overall biodegradability velocity, the biodegradability of the various hydrocarbon chemical classes can be classified as follows:

$$(V_{bio})_{C14-sat} = (V_{bio})_{max}$$

$$(V_{bio})_{C14-aro} = 0.6 \times (V_{bio})_{max}$$

$(V_{bio})_{C14+n} = (V_{bio})_{max}$ $(V_{bio})_{C14+iso} = (0.8) \times (V_{bio})_{max}$ $(V_{bio})_{C14+cyclanes} = (0.3) \times (V_{bio})_{max}$ $(V_{bio})_{C14+aro} = (0.1) \times (V_{bio})_{max}$ $(V_{bio})_{C14+nso} = (0.0) \times (V_{bio})_{max}$ The second term allowing $V_c$ to be defined accounts for the hydrocarbon accessibility in the porous medium, i.e. their capacity to be accessible to bacteria (for example, the $C_6$-$C_{14}$ aromatics are the most water soluble hydrocarbons, they therefore have the highest accessibility).

$(V_{accès})_{C14-aro} = (V_{accès})_{max}$ $(V_{accès})_{C14-sat} = 0.4 \times (V_{accès})_{max}$ $(V_{accès})_{C14+chains} = (0.2) \times (V_{accès})_{max}$ $(V_{accès})_{C14+cyclanes} = (0.2) \times (V_{accès})_{max}$ $(V_{accès})_{C14+aro} = (0.3) \times (V_{accès})_{max}$ $(V_{accès})_{C14+nso} = (0.0) \times (V_{accès})_{max}$ Thus, the second term $V_c$ for the various chemical classes is:

$V_C C_{14-sat} = (V_{bio})max \times 0.4 \times (V_{accès})max$ $V_C C_{14-aro} = 0.3 \times (V_{bio})max \times (V_{accès})max$ $V_C C_{14+}n = (V_{bio})max \times 0.3) \times (V_{accès})max$ $V_C C_{14+}iso = 0.7 \times (V_{bio})max \times 0.2 \times (V_{accès})max$ $V_C C_{14+}cyclanes = 0.4 \times (V_{bio})max \times 0.2 \times (V_{accès})max$ $V_C C_{14+}aro = 0.15 \times (V_{bio})max \times 0.3 \times (V_{accès})max$ $V_C NSO = 0$.

Thus, by taking account of all the terms $(V_{max} = (V_{bio})max \times (V_{accès})max)$, the overall biodegradation velocities (V) for the various chemical classes are as follows:

$VC_{14-sat} = (V_{bio})max \times 0.4 \times (V_{accès})max = 0.4 \times V_{max}$ $VC_{14-aro} = 0.3 \times (V_{bio})max \times (V_{accès})max = 0.3 \times V_{max}$ $VC_{14+}n = (V_{bio})max \times 0.3) \times (V_{accès})max = 0.2 \times V_{max}$ $VC_{14+}iso = (0.7) \times (V_{bio})max \times 0.2 \times (V_{accès})max = 0.18 \times V_{max}$ $VC_{14+}cyclanes = (0.4) \times (V_{bio})max \times (0.2) \times (V_{accès})max = 0.08 \times V_{max}$ $VC_{14+}aro = (0.15) \times (V_{bio})max \times (0.3) \times (V_{accès})max = 0.05 \times V_{max}$ $VNSO = 0$.

4—Estimation of the Evolution of the Hydrocarbon Composition

The proportion of each chemical class after biodegradation is determined by applying the reaction scheme defined in stage 3 to the proportions of each chemical class estimated in stage 2.

Variants/Applications

The main range of application is the prediction of the amount of oil after a biological alteration in basin models. Thus, according to an embodiment, the API degree and the viscosity of the hydrocarbons thus degraded are determined by means of correlations between the API degree and the saturated hydrocarbon decrease, or according to the concentration in NSO compounds.

According to another embodiment, the production of associated gases of biological origin ($CH_4$, $CO_2$ and $H_2S$) and, eventually, the acidity of the crudes are determined. The method thus contributes towards a better economic assessment of the petroleum reservoir and therefore allows decisions to be made as regards drilling.

According to another embodiment, the compositional and reaction schemes can also be applied to the estimation of the biodegradation of an oil during production (reservoir scale).

These three evaluations (oil quality, acid gas or methane production and biodegradation during production) allow each to determine whether it is appropriate to develop a petroleum reservoir and, if so, to determine the development conditions (drilling location, mud pressure, drilling equipment . . . ).

According to another embodiment, the compositional and reaction schemes can also be applied to the evaluation of the biodegradation of hydrocarbons in polluted sites.

The method thus allows to determine the composition of the fluids present in a porous medium as a result of biodegradation. These fluids correspond, on the one hand, to biodegraded hydrocarbons and, on the other hand, to the metabolites produced during this biodegradation, and notably associated gases of biological origin: $CH_4$, $CO_2$ and $H_2S$.

The invention claimed is:

1. A method of determining a composition of fluids present in a porous medium after biodegradation, characterized in that it comprises: defining a biodegradation compositional scheme from at least the following chemical classes: CO.sub.2, n-saturated H.sub.2S, C.sub.1, C.sub.2-C.sub.4, C.sub.6-C.sub.14 and iso-saturated C.sub.6-C.sub.14, cyclo-saturated C.sub.6-C.sub.14, C.sub.6-C.sub.14 aromatics, n-saturated C.sub.14+, iso-saturated C.sub.14+, cyclo-saturated C.sub.14+, C.sub.14+ aromatics, NSOs, determining an amount of each one of said chemical classes contained in said fluids before biodegradation, defining a biodegradation reaction scheme wherein said chemical classes react with electron acceptors and wherein it is imposed that said classes react simultaneously with a first electron acceptor having the highest oxydoreduction potential, according to different reaction velocities and up to depletion of said first acceptor in the medium, then they react sequentially towards the other electron acceptors according to the same principle, determining said reaction velocities of each one of said chemical classes according to at least:—the potential concentration of the chemical classes in water;—their intrinsic biodegradability;—their reactivity to said electron acceptors;—the temperature of the medium; and—the residence time of said fluids within the medium, and determining the composition of said fluids by assessing an amount for each one of said chemical classes of the compositional scheme by applying the reaction scheme.

2. A method as claimed in claim 1, wherein said electron acceptors are selected from among the following acceptors: $O_2$, $NO_3$, $SO_4$ and $H_2O$.

3. A method as claimed in claim 1, wherein said reaction velocities are defined by a product of a first term (R.sub.t) allowing an effect of residence time in the porous medium to be taken into account, a second term (R.sub.T) allowing an effect of temperature to be taken into account and a third term (V.sub.c) allowing accessibility and the intrinsic biodegradability of each chemical class to be taken into account.

4. A method as claimed in claim 3, wherein first term $R_t$ represents a biodegradation efficiency and it is determined by means of a first evolution curve of said efficiency $R_t$ as a function of the residence time in the medium.

5. A method as claimed in claim 4, wherein said first curve is an exponential function of time, where said efficiency $R_t$ is above 95% beyond about 2000 years.

6. A method as claimed in claim 3, wherein second term $R_T$ represents a biodegradation efficiency and it is determined by means of a Gaussian evolution curve of said efficiency $R_T$ as a function of the temperature in the medium.

7. A method as claimed in claim 6, wherein said Gaussian curve is centered on a temperature of about 30° C. and it is equated to zero for 0° C. and about 70° C.

8. A method as claimed in claim 3, wherein third term $V_c$ is determined by considering that the intrinsic biodegradability velocity of the n-saturated, cyclo-saturated, and iso-saturated $C_6$-$C_{14}$ is higher than that of the other classes, and by considering that a maximum accessibility velocity of the $C_6$-$C_{14}$ aromatics is higher than that of the other classes.

9. A method as claimed in claim 3, wherein said reaction velocities are defined by: $V$ $C_{14^-}$sat=0.4.times.$V_{max}$ $V$ $C_{14^-}$aro=0.3.times.$V_{max}$ $V$ $C_{14^+}$n=0.2.times.$V_{max}$ $V$ $C_{14^+}$iso=0.18.times.$V_{max}$ $V$ $C_{14^+}$cyclanes=0.08.times.$V_{max}$ $V$ $C_{14^+}$aro=0.05.times.$V_{max}$ $V$ NSO=O where $V_{max}$ is the maximum biodegradation velocity defined by the product of a maximum intrinsic biodegradability velocity by a maximum accessibility velocity.

10. A method as claimed in claim 1, wherein said medium is a petroleum reservoir, and an amount of acid gas produced upon biodegradation is deduced from said composition of the fluids in order to determine development conditions for said petroleum reservoir.

11. A method as claimed claim 1, wherein said medium is a petroleum reservoir, and an amount of methane produced upon biodegradation is deduced from the composition of the fluids in order to determine development conditions for said petroleum reservoir.

\* \* \* \* \*